(12) United States Patent
Letzelter et al.

(10) Patent No.: US 9,493,913 B2
(45) Date of Patent: Nov. 15, 2016

(54) METHOD FOR STABILIZING THE WHITENESS OF FLUORESCENT WHITENING AGENT(S)(FWA) INCLUDED IN SURFACE-TREATMENT SIZE/COATING SLIP FOR PAPER AND OF SURFACE-TREATMENT LAYERS FORMED THEREOF

(75) Inventors: Philippe Letzelter, Iggesund (SE); Johan Lindgren, Iggesund (SE)

(73) Assignee: HOLMEN AB, Stockholm (SE)

( * ) Notice: Subject to any disclaimer, the term of this patent is extended or adjusted under 35 U.S.C. 154(b) by 206 days.

(21) Appl. No.: 12/304,945

(22) PCT Filed: Jun. 14, 2007

(86) PCT No.: PCT/SE2007/000585
§ 371 (c)(1),
(2), (4) Date: Dec. 15, 2008

(87) PCT Pub. No.: WO2007/145577
PCT Pub. Date: Dec. 21, 2007

(65) Prior Publication Data
US 2009/0281221 A1    Nov. 12, 2009

(30) Foreign Application Priority Data

Jun. 15, 2006   (SE) ...................................... 0601324

(51) Int. Cl.
*B32B 29/06* (2006.01)
*D21H 21/30* (2006.01)
(Continued)

(52) U.S. Cl.
CPC .............. *D21H 21/30* (2013.01); *B32B 29/06* (2013.01); *B32B 2255/12* (2013.01); *B32B 2255/24* (2013.01); *C07C 31/26* (2013.01); *C11D 3/42* (2013.01); *D21H 17/06* (2013.01); *D21H 17/36* (2013.01); *D21H 19/12* (2013.01);
(Continued)

(58) Field of Classification Search
CPC ........ C07C 31/26; C11D 3/42; D21H 17/06; D21H 17/36; D21H 19/12; D21H 19/46; D21H 19/52; D21H 19/62; D21H 19/60; D21H 21/16; D21H 21/30
See application file for complete search history.

(56) References Cited

U.S. PATENT DOCUMENTS 3,970,647 A   7/1976  Balzer et al.
5,976,410 A   11/1999 Rohringer et al.
(Continued)

FOREIGN PATENT DOCUMENTS

WO   WO 96/00221 A1   1/1996
WO   WO 98/42685 A1   10/1998
(Continued)

OTHER PUBLICATIONS

"Surface Application of Paper Chemicals," Brander J. and Thorn, I., eds. Champman & Hall, 1997.*
(Continued)

*Primary Examiner* — Richard A Huhn
(74) *Attorney, Agent, or Firm* — Knobbe Martens Olson & Bear LLP

(57) ABSTRACT

The present invention relates to a method for increasing the whiteness stability of fluorescent whitening agent(s) (FWA) included in surface-treatment size/coating slip for paper and of the surface-treatment layers formed thereof. The method is characterized in that sorbitol is charged to the size/coating slip as a carrier.

9 Claims, 1 Drawing Sheet

(51) Int. Cl.
| | |
|---|---|
| D21H 19/62 | (2006.01) |
| D21H 19/60 | (2006.01) |
| D21H 19/12 | (2006.01) |
| D21H 21/16 | (2006.01) |
| C11D 3/42 | (2006.01) |
| D21H 19/52 | (2006.01) |
| D21H 17/36 | (2006.01) |
| C07C 31/26 | (2006.01) |
| D21H 17/06 | (2006.01) |
| D21H 19/46 | (2006.01) |

(52) U.S. Cl.
CPC ............. *D21H 19/46* (2013.01); *D21H 19/52* (2013.01); *D21H 19/60* (2013.01); *D21H 19/62* (2013.01); *D21H 21/16* (2013.01)

(56) References Cited

U.S. PATENT DOCUMENTS

| | | | | |
|---|---|---|---|---|
| 6,008,289 | A | * | 12/1999 | Konig et al. .................. 524/591 |
| 6,133,215 | A | * | 10/2000 | Zelger et al. .................. 510/326 |
| 6,620,294 | B1 | * | 9/2003 | Jokinen ................ C08K 5/0041 162/135 |
| 2002/0156179 | A1 | | 10/2002 | Egraz et al. |
| 2003/0236326 | A1 | | 12/2003 | Drenker et al. |

FOREIGN PATENT DOCUMENTS

| | | | |
|---|---|---|---|
| WO | 00/69977 A1 | 11/2000 | |
| WO | WO 01/44210 A1 | 6/2001 | |
| WO | WO 2004/005617 A1 | 1/2004 | |
| WO | 2004/050994 A1 | 6/2004 | |
| WO | WO 2005068597 A1 * | 7/2005 | ............... C11D 3/42 |
| WO | 2005/088012 A1 | 9/2005 | |
| WO | 2006/045714 A1 | 5/2006 | |

OTHER PUBLICATIONS

R. L. Broggi, et al., "Study of an alkaline bath for tin deposition in the presence of sorbitol and physical and morphological characterization of tin film", Journal of Applied Electrochemistry, 2006, pp. 403-409, vol. 36.

International Search Report and Written Opinion dated Sep. 13, 2007 for PCT Application No. PCT/SE2007/000585, filed Jun. 14, 2007.

International Preliminary Report on Patentability dated Dec. 16, 2008 for PCT Application No. PCT/SE2007/000585, filed Jun. 14, 2007.

* cited by examiner

METHOD FOR STABILIZING THE WHITENESS OF FLUORESCENT WHITENING AGENT(S)(FWA) INCLUDED IN SURFACE-TREATMENT SIZE/COATING SLIP FOR PAPER AND OF SURFACE-TREATMENT LAYERS FORMED THEREOF

CROSS REFERENCE TO RELATED APPLICATION

This application is a National Stage of International Application No. PCT/SE2007/000585 filed Jun. 14, 2007, claiming priority based on Swedish Patent Application No. 0601324-7, filed Jun. 15, 2006, the contents of all of which are incorporated herein by reference in their entirety.

TECHNICAL FIELD

The present invention concerns improvement in the whiteness stability of fluorescent whitening agents included in surface-treatment agents for paper in the form of size and coating slip and of surface-treatment layers formed of said agents. Fluorescent whitening agents (FWA) were previously often denominated optical brightening agents (OBA). This agent has the property that it absorbs ultraviolet light (having a wavelength of <380 nm) invisible to the human eye and re-emits the light at wavelengths that are visible to the human eye. The re-emission is marked within the wavelength range of 430-470 nm, where the light has a blue hue. This process is perceived by the human eye as if the brightness and/or the whiteness of the object in question, which has been supplied or covered with FWA, have increased. Fluorescent whitening agents are chemical compounds of organic type. Stilbene derivatives, i.e., chemical compounds that, among other things, contain two benzene rings, are usual. A more detailed description of said agents is available in the material being referenced to and commented on further on in this document. For a thorough study of the chemical structure of different whitening agents, reference is made to textbooks and encyclopedias.

A wide field of application of FWA is the pulp and paper industry. The agent may be mixed into the proper paper as well as be applied to the surface of the paper in various ways, which technical field the present invention comprises. By definition, cardboard (paperboard) falls within the concept of paper, and here it is established that cardboard (paperboard) is a special case and a special type of paper.

PRIOR ART

It is important for paper and accordingly also for cardboard (paperboard) to be capable of resisting light-induced ageing. For surface-treated, for instance, surface-sized and/or coated, products, the fastness to light/of whiteness may be divided into two parts, one part depending on the pulp fibres (of one type or usually several types) that the product is made up of, and one part that depends on the ageing of the surface material. The latter applies above all to surface materials that contain FWAs. It has turned out that FWAs, as a group of compounds, are unstable. With unstable is meant that the property described above deteriorates over time, i.e., decays, possibly all the way down to zero. The most common preparation form is that the agent is solved in a liquid, and water is a useful and common liquid. For instance, a dilution of a whitening-agent aqueous solution may cause instability. In surface sizing and coating, which are the two most common ways of surface treatment of paper, FWA, as has been indicated previously, is usually included in the size and the coating slip, respectively, that is applied to the paper. After application of the surface size (having a very low content of solids) and/or the coating slip (having a very high content of solids, such as 60-70%), the paper is allowed to dry so that the agent is included in a solid, thin layer on the paper. From practice as well as the literature, it is known that the stability of the agent deteriorates and that it even breaks down by such factors as daylight (the ultraviolet radiation) heat and air humidity.

In order for the FWA to give the desired effect, it has to be supplied with a carrier. Accordingly, this applies to a surface size as well as to a coating slip. Furthermore, the carrier has the property that it, to a certain extent, protects against light-induced ageing, which FWA is susceptible to, as has been indicated. Examples of carriers that are used by routine today are carboxymethyl cellulose (CMC), polyvinyl alcohol (PVA) and starch in different forms.

By the admixture of miscellaneous chemicals to, for instance, a coating slip, it has turned out to be possible to limit the light-induced ageing of the coating layer. This is good, per se, but it has simultaneously turned out that the chemicals in question often impairs the structure of the coating slip, which makes the usage of the coating slip more difficult or impossible in known application methods. As is known, today the speed of the material web in the coating unit in paper as well as paperboard machines is high, and something that constantly is attempted to be increased, and then it is important that the coating slip always works well so that it without any problems can be applied to the material web and remains thereon to the desired extent. The situation described above applies to, for instance, the size and coating slip additives disclosed in the Swedish patent specification 524 471 (0203602-8). These consist of an organic acid, which contains an aromatic group and/or can be esterified internally forming lactone, or the salt of the acid (additive A) and a reducing chemical (additive B). An example of A is ascorbic acid and the relatives thereof (or the salt), and an example of B is a chemical containing hydrogen sulphite ($HSO_3^-$) and/or sulphite ($SO_3^{2-}$).

In the international (PCT) patent application WO 2005/068597, there is described a mixture of three particular, fluorescent whitening agents, which are stated to inherently have the desirable property of withstanding light-induced ageing. On page 10, second paragraph, in the patent application, for instance, the following is stated:

"In one further aspect of the invention, the mixture of the compounds of formulae (1a), (1b) and (1c) provide a method for increasing the SPF (Sun Protection Factor) rating or for the fluorescent whitening of a textile fibre material, comprising treating the textile fibre material with 0.05 to 5° by weight, based on the weight of the textile fibre material, with one or more mixtures of the compounds of formulae (1a), (1b) and (1c) of the invention, as previously defined."

Said three particular fluorescent whitening agents can also be used in surface size and coating slip for the treatment of paper. Most space in the patent application is given to the structural formulae, i.e., the chemical structure, of said three fluorescent whitening agents. However, it is mentioned that it is possible to produce an aqueous solution consisting of, in addition to said agents, a plurality of "auxiliaries". A large number of auxiliaries are listed including pigments, dispersants, water-retention aids, binders, thickeners and carriers. As examples of carriers in, for instance, a coating slip, polyethylene glycol, soybean protein, casein, carboxymethyl cellulose, natural or modified starch, chitosan or derivatives of, or particularly, polyvinyl alcohol, are mentioned. As examples of "water-retention aids", ethylene glycol, glycerol, sorbitol and biocides are mentioned. Coating slips in their entirety are mentioned at several places in the patent application, for instance, right at the bottom of page 7 and at the top of page 8 as well as in the embodiment examples 14-33. The ingredient always being dominant quantity-wise in coating slips in this connection, i.e., the pigment, is of course mentioned.

SUMMARY OF THE INVENTION

Technical Problem

As is seen from the previously mentioned, there are ways to increase the stability as regards the brightness/whiteness of the coating layers of paper that contain fluorescent whitening agents (FWA). However, it has turned out difficult to find agents, i.e., chemicals, that on one hand increase said stability and on the other hand leave, for instance, coating slips unaffected as regards usefulness and runnability in, for instance, industrial coating.

The Solution

The present invention solves this problem and relates to a method for increasing the whiteness stability of fluorescent whitening agent(s) (FWA) included in surface-treatment size/coating slip for paper and of surface-treatment layers formed thereof, characterized in that sorbitol is charged to the size/coating slip as a carrier.

As regards the fluorescent whitening agent, any known one can be used. A plurality of whitening agents in a mixture may also be used. The charge of whitening agent may vary. In coating slips, the charge is given in parts by weight based on 100 parts by weight of pigments included in the coating slip. The charge is often within the range of 0.1-1 part by weight and most commonly is a charge of 0.2-0.5 parts by weight. In surface sizes, the charge is given in percent of absolutely dry size, and a suitable charge is 0.05-15%, preferably 0.1-0.5%. In the concluding embodiment example, a fluorescent whitening agent is described more in detail.

It is possible to add sorbitol as a sole carrier, but also to add, in addition to sorbitol, at least one additional carrier. As has been indicated previously, there is a large number of carriers available, and any of these carriers may be used together with sorbitol. Advantageously, at least one of the following carriers can be used together with sorbitol; carboxymethyl cellulose, polyvinyl alcohol and starch.

Coating slips may have a highly varying formulation, and as a consequence of this, a large number of chemicals may be included in the coating slip and then in varying quantities. However, there are coating slips that contain anything from a few ingredients to a very large number of ingredients. In addition to fluorescent whitening agent, a coating slip may contain a few or more, possibly all, of the following chemical types: pigments, binders, carriers, hardeners, dispersants, thickeners and water-retention aids. Quantity-wise, the pigment is dominating. This may be calcium carbonate, a natural one including ground marble, chalk and talc and precipitated such (PCC), alone or in a mixture with aluminium or magnesium silicate, such as kaolin and "China clay" and furthermore barium sulphate, satin white and titanium dioxide. The pigment may, as pointed out above, be entirely free from calcium carbonate. Furthermore, there are white organic pigments.

The sorbitol in the form of a carrier is charged to the coating slip in an amount of 0.5-10 parts by weight, based on 100 parts by weight of pigments. A preferred admixture is 14 parts by weight, based on 100 parts by weight of pigments.

The coating slip can be applied to the paper according to any known coating method. The coating slip may be applied to one side of the paper or both sides thereof and in the form of a single layer or double layer or triple layer. The grammage of a coating layer may vary all the way from approx. 7 $g/m^2$ to approx. 50 $g/m^2$. In the application of a plurality of coating layers, the amount of coating slip for each layer is often lower than the amount of coating slip applied in one single layer.

The surface size may also have a highly varying structure, and as a consequence of this, a number of chemicals may be included in the size and then in varying amounts. In contrast to a coating slip that has a very high content of solids, for instance, 60-70%, a surface size has usually a very low content of solids and it can be within the range of 0.5-15%. In addition to fluorescent whitening agent, the surface size may contain one or more of the following chemicals; starch, carboxymethyl cellulose, latex, carrier, pigment and hydrophobic agent. The application of surface size may vary from such a low amount as 1 $g/m^2$ up to approx. 10 $g/m^2$.

Since the surface size not always, but rather as an exception, contains pigments, it is not possible to couple the admixture of the carrier sorbitol to 100 parts by weight of pigments. Therefore, it is selected to couple the admixture of sorbitol to the amount of absolutely dry size and it amounts to 1-50%, preferably 2-10%, of the absolutely dry surface size.

Traditionally, size presses have been used to apply surface size to the paper. The size press is usually placed so far forward in the drying portion of the paper/paperboard machine that the paper has had time to dry to a dry solids content of approx. 95%. Recently, one has increasingly abandoned traditional size presses and turned to coating-like equipment, for instance, blade coaters and bar coaters.

As regards coating slips in particular, they are affected by too a large admixture of carriers because of their thickening effect. The usefulness and runnability of the coating slip are, among other things, coupled to the viscosity of the coating slip. The concept runnability involves, among other things, that the coating slip should be pumpable. There are a plurality of different ways to determine the viscosity of a coating slip. Such a measurement, where low shear rates are used, is called Brookfield viscosity and the denomination is cP. It has turned out that if the viscosity of the coating slip measured according to Brookfield exceeds 2500 cP, the runniability of the coating slip is markedly deteriorated.

For that reason, the admixture amount of the most common carriers has to be limited. As regards, for instance, carboxymethyl cellulose (CMC), it is fine to charge 0.5 parts by weight, while already 1 part by weight gives much too high a Brookfield viscosity. As regards polyvinyl alcohol, which is a usually occurring carrier, it is fine to charge 2 parts by weight, but one should be careful to exceed that admixture. With the carrier according to the invention, i.e., sorbitol, it has very surprisingly turned out that the relationship is the opposite, i.e., the Brookfield viscosity of the coating slip decreases with increased admixture of sorbitol.

Advantages

The embodiment example accounted for further on in this publication shows that if sorbitol is used as a carrier in a coating slip containing fluorescent whitening agents that is applied to cardboard (paperboard), an increasing admixture of sorbitol in the coating layers on the cardboard (paperboard) causes the initial CIE whiteness of the product to increase as well as the whiteness stability to increase, i.e., the decrease of the whiteness of the cardboard (paperboard) depending on light-induced ageing is efficiently inhibited.

This, i.e., the admixture of sorbitol, does not take place at the expense of the structure and rheology of the coating slip and ultimately the usefulness and runnability of the coating slip, but rather the contrary. It has for certain been established that the runnability properties of the coating slip are not deteriorated. As regards the critical Brookfield viscosity of the coating slip, which must not be too high, an increasing admixture of sorbitol, which is good from an initial whiteness point-of-view as well as from a whiteness stability point-of-view according to the above, results in decreased viscosity. There is no risk that the viscosity of the coating slip should become too low upon admixture of a very high admixture amount of sorbitol (in comparison with admixture of conventional carriers), since there are always thickeners available.

THE BEST EMBODIMENT

Figure 1:
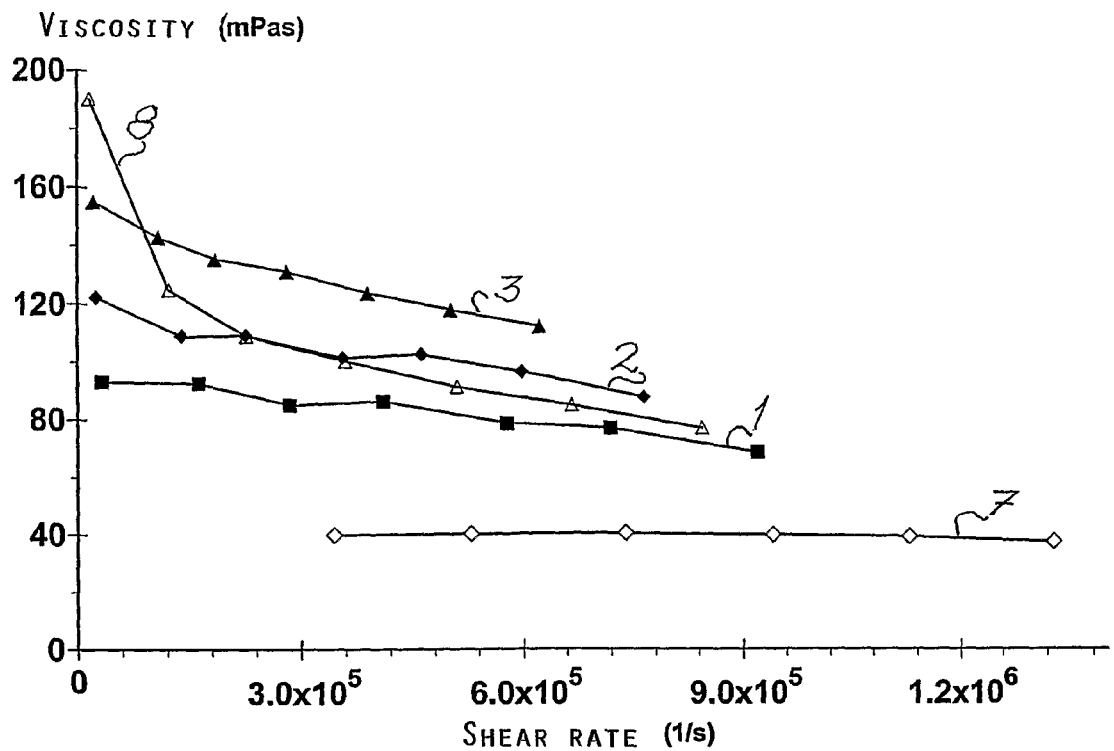
In FIG. 1, it is shown how the capillary viscosity of coating slips varies with the shear rate when using traditional carriers in the coating slip.

In the following, the certain parts of invention are described more in detail and this while simultaneously reporting tests made in a laboratory.

Example 1

In the laboratory of a paperboard mill, the following tests were made.

Solid paperboard of standard quality, having a grammage of 265 g/m$^2$, was sampled at the mill. No ligiin-containing pulp fibres were used in the different layers, which amounted to a number of five. Only bleached sulphate pulp was included in the different pulp stocks including softwood pulp as well as hardwood pulp. All pulps had a brightness exceeding 88% ISO.

In a blade coater of pilot-plant magnitude in the laboratory, coating slips were applied in three runs on one side of the paperboard. In one end of the coater, a reel of paperboard was applied having a width of 60 cm and a diameter of 180 cm. The paperboard web was unreeled and brought through the coater in three runs.

The coating slip formula of the precoating and intermediate coating consisted of:
100 parts by weight of calcium carbonate in the form of ground marble (of the Hydrocarb type)
12 parts by weight of latex (binder)
0.9 parts by weight of polyvinyl alcohol (works as a carrier)
0.6 parts by weight of synthetic thickener ("co-binder")
0.12 parts by weight of hardener in the form of ammonium zirconium carbonate (of the Bacote type)
0.25 parts by weight of FWA (of the Blankophor® P Fluessig type).

The dry solids content of the coating slip was 67%. The precoating layer had a grammage of 10 g/m$^2$ and the intermediate coating layer of 7 g/m$^2$.

The coating slip formula of the top coating consisted of:
70 parts by weight of calcium carbonate in the form of ground marble (of the Hydrocarb type)
30 parts by weight of clay
16 parts by weight of latex (binder)
0.72 parts by weight of polyvinyl alcohol (works as a carrier)
0.4 parts by weight of synthetic thickener ("co-binder")
0.17 parts by weight of hardener in the form of ammonium zirconium carbonate (of the Bacote type)
0.20 parts by weight of FWA (of the Blankophor® Fluessig type).

The dry solids content of the coating slip was 66%.

The top coating layer had a grammage of 8 g/m$^2$, which means that the total grammage for the three coating layers was 10+7+8=25 g/m$^2$.

Each coating run consisted of four tests depending on the fact that in each run, the cardboard (paperboard) was coated with the coating slips described above plus that said coating slips were supplemented with the carrier according to the invention, i.e., sorbitol, which was added in an amount of 1, 2 and 3 parts by weight. This means that in the first experiment, a smaller amount of polyvinyl alcohol was used as a sole carrier (reference), and in the three further experiments, the coating slip was, in addition to the smaller amount of polyvinyl alcohol as a carrier, also supplied with sorbitol as a carrier.

In the experiments made, no problems arose with any of the coating slips according to the invention, i.e., those that contained sorbitol, from a structural and rheological point-of-view, which in turn have an effect on the usability and runnability of the coating slip. As regards this circumstance, no difference at all was found between the reference coating slip and the three coating slips according to the invention.

After the paperboard web had finally dried, the same was converted into sheets of A4 size.

Next, the coated side of the cardboard (paperboard) sheets was exposed to light in a test chamber of the Suntest XLS+ type for a period of 8 h. The light is generated by a Xenon lamp, the light of which resembles the light of the sun. However, certain light wavelengths have to be filtered away. This is effected by means of filters of glass that transmit ultraviolet (UV) light. In the experiments, a filter was used that filters away light having a wavelength of less than 320 nm, which light resembles the light in a show-window. The power of the Xenon lamp was 600 W. One hour of exposure to light in the test chamber corresponds to a space of time of approximately 3.6 days in daylight.

A number of interruptions in the exposure to light of the cardboard (paperboard) samples were made in order to measure the whiteness thereof. The measurement was made using an Elrepho SF 450 from Datacolor International. A measurement was also made on the cardboard (paperboard) samples before the same were put into the test chamber. The whiteness measured was CIE whiteness. CIE, which stands for "Commission Internationale de l'Eclairage", specifies the spectral energy distribution of a standard light. The measurement results are seen in Table 1 below.

TABLE 1

| Time of light exposure in hours | CIE whiteness Parts by weight of sorbitol | | | |
|---|---|---|---|---|
| | 0* | 1 | 2 | 3 |
| 0 | 117.8 | 120.1 | 121.4 | 123.5 |
| 0.5 | 100.7 | 108.6 | 114.5 | 119.0 |
| 1 | 96.7 | 104.6 | 111.0 | 116.1 |
| 2 | 93.5 | 101.0 | 107.7 | 113.1 |
| 4 | 90.2 | 97.0 | 103.8 | 109.3 |
| 8 | 86.2 | 91.7 | 98.0 | 103.7 |

*The test series where no sorbitol has been added to the coating slip constitutes the reference samples. In said coating slips, only polyvinyl alcohol is used as a carrier. Note that in all other coating slips, i.e., in the pre-, intermediate and top coating slip, sorbitol has been charged in an amount corresponding to the parts by weight given in the table.

As is seen, admixture of sorbitol as a carrier in the coating slip causes the initial whiteness of the cardboard (paperboard), i.e., before the cardboard (paperboard) has been subjected to exposure to light, to increase and it increases clearly with increasing admixture amount of sorbitol.

As regards the whiteness stability, it is improved markedly by virtue of admixture of sorbitol. The whiteness of the reference sample dropped 31.6 units after 8 hours of exposure to light, while the corresponding values for the admixture of 1, 2 and 3 parts by weight of sorbitol were 28.4 and 23.4 and 19.8 units, respectively. As is seen, the whiteness stability is clearly improved with increasing admixture of sorbitol in the coating slip. There is no reason to believe that the whiteness stability has an optimum at an admixture of 3 parts by weight of sorbitol, but it is more likely that the whiteness stability is further improved at even larger admixtures of sorbitol. The upper admixture limit of sorbitol is assumed to be dependent upon the runnability of the coating slip and possibly the cost increase with increasing admixture of sorbitol.

As has been pointed out previously, it is not enough to make sure that, by admixture of, for instance, miscellaneous chemicals, the fluorescent whitening agent in, for instance, the coating layer(s), is stabilized, but the coating slip in itself also has to have special qualities, for instance, be useful and runnable in industrial coating.

Therefore, a number of coating slips have been produced in the laboratory that have been tested foremost as regards the viscosity properties thereof, since among those skilled in the art, it is apparent that there is a relationship between the viscosity properties of the coating slip and the usefulness/runnability thereof.

The base of all coating slips was by the following chemicals:
100 parts by weight of calcium carbonate of the Carbital type
12 parts by weight of latex (binder)
0.12 parts by weight of hardener in the form of ammonium zirconium carbonate (of the Bacote type)
0.25 parts by weight of FWA (of the Blankophor® Fluessig type).

What was varied in the coating slips and is reported in Table 2 below was a synthetic thickener ("co-binder") as well as the carriers polyvinyl alcohol (PVA), carboxymethyl cellulose (CMC) and sorbitol.

TABLE 2

| Coating slip | Parts by weight | | | |
|---|---|---|---|---|
| | Thickener | PVA | CMC | Sorbitol |
| 1 | 0.6 | 1 | 0 | 0 |
| 2 | 0.6 | 1.5 | 0 | 0 |
| 3 | 0.6 | 2 | 0 | 0 |
| 4 | 0.6 | 1 | 0 | 1 |
| 5 | 0.6 | 1 | 0 | 2 |
| 6 | 0.6 | 1 | 0 | 3 |
| 7 | 0 | 1 | 0.5 | 0 |
| 8 | 0 | 1 | 1 | 0 |

As is seen, one of the carriers is present in all coating slips, viz. PVA. Six measurements were made on the coating slips, viz. pH (standard), dry solids content according to SCAN-P 39-80, the water-retention capacity, and three viscosity measurements. The four last mentioned measuring methods are briefly described below.

The water-retention capacity was determined according to a method denominated ÅAGWR. This is an abbreviation of "Åbo Akademi Gravimetric Water Retention" and is explained by the method originally being developed at Åbo Akademi in Finland. The analysis method gives a measure of how much water that is filtered (pressed) out of a coating slip at a pressure of 0.4 bar for a period of 2 minutes. The measurement instrument is manufactured by a company named Gradek, and consists of a sample cylinder that is open in the lower part thereof. A filter paper is weighed and placed on a plastic shim. On top of the same, a membrane filter of a certain type (OSMONICS Polycarbonate 47 mm/5.0 micron) is placed. On top of the membrane filter, the sample cylinder is placed, the upper part of which contains a piston connected to compressed air. 10 ml of the coating slip is sucked up into a plastic syringe and the sample is inserted into the sample cylinder. The piston is then allowed to be pressed against the sample at a pressure of 0.4 bar for 2 min. A part of the water present in the coating slip is pressed through the membrane filter and down into the filter paper. The filter paper is weighed again and the difference between the weights is converted, by means of the area of the filter paper, into the amount of water in grams per square meter given off by the coating slip.

One of the viscosity measuring methods is called Brookfield. In this measuring method, an instrument is used denominated Anton Paar DV-IPR. Generally, the method may be described in such a way that a rotating measuring body is immersed into a liquid and the rotary resistance is measured. The viscosity is a measure of how viscous a liquid is. The higher the viscosity, the more viscous the liquid is. The viscosity is measured in centiPoise (cP). When measurements are made on a coating slip, at least 500 ml of coating slip is applied in a 600 ml glass beaker. The measuring body, which is cylindrical and is called bob or spindle, is brought down into the coating slip. There are bobs or spindles of different sizes and a certain one was used to measure the viscosity of just one coating slip. In the measurement, the bob is set into rotation, which gives a shear rate (1/s=reciprocal seconds) in the gap between the beaker and the bob. The character of the sample determines how large shear stress (Pa) that arises as a consequence of said rotation, i.e., shear rate. The ratio between the shear stress and the shear rate constitutes the viscosity (mPa·s, which can be transformed into cP) of the coating slip at the temperature and the shear rate in question. In this measuring method, comparatively low shear rates are used.

Another similar viscosity measuring method is called Hercules HI-shear. Also here, a metal body is immersed into a measurement cup including a coating slip. The metal body is brought into rotation at higher shear rates in comparison with the Brookfield method, which may be represented as intermediate shear rates. The dimension of the viscosity is, in accordance with what has been described above, mPa·s, i.e., milllipascal seconds.

In order to reach pronouncedly high shear rates, which is not possible to attain in the two described measuring methods, a capillary viscometer of the ACASystems type was used. In the same, the coating slip is pressed out through small thin capillaries of metal under very high pressure. The coating slip that is pressed out is automatically weighed by the instrument and a computer program calculates the capillary viscosity of the coating slip in the unit or dimension of mPa·s. When the coating slip is pressed through a capillary, it is subjected to a shear rate and as a result also to a shear stress. In this measuring method, high shear rates are used, or expressed in another way, the coating slip is subjected to high shear rates, which is also indicated in the introduction of this paragraph.

In Table 3 below, the results of measurements made are specified (except the results of the measurements regarding the capillary viscosity of the coating slip, which is depicted in curve form in FIGS. 1 and 2).

TABLE 3

| Coating slip | pH | Dry solids content % | ÅAGWR g/m² | Hercules viscosity at 17000 recipr. sec mPa · s | Brookfield viscosity cP |
| --- | --- | --- | --- | --- | --- |
| 1 | 8.7 | 67.0 | 89 | 80.2 | 1650 |
| 2 | 8.6 | 67.0 | 45 | 95.0 | 2180 |
| 3 | 8.8 | 66.7 | 43 | 107.9 | 2250 |
| 4 | 8.6 | 67.1 | 59 | 74.6 | 1350 |
| 5 | 8.6 | 67.0 | 59 | 69.2 | 1350 |
| 6 | 8.6 | 67.0 | 53 | 63.6 | 1040 |
| 7 | 8.7 | 67.0 | 75 | 48.8 | 1290 |
| 8 | 8.3 | 67.1 | 49 | 149.0 | 6300 |

As is seen, the variation of the pH value of the different coating slips is almost non-existing. The same applies to the variations of the dry solids content.

As regards the water-retention capacity of the coating slips, the variation is large. It is good to have a low value, because it means that the coating slip releases small amount of water via the interface coated slip and support, i.e., the paper including the cardboard (paperboard). This has a practical importance in the coating operation. In, for instance, blade coating, the coating slip is applied to the forwardly running paper web in a certain fixed position, and in another fixed position further on in the transport direction of the paper, the surplus of coating slip is scraped off, which drips down into a subjacent tank. The greater the amount of water released by the coating slip and absorbed by the paper during said distance, the greater amount of chemicals dissolved in the water is transferred from the coating slip to the paper, causing an increasing divergence between the chemical composition of the applied coating slip and the chemical composition of the recycled coating slip. This is of importance because coating slips are produced batch-wise as well as are consumed batch-wise. Even if this property of the coating slip is of importance, it has to be subordinated to the viscosity properties of the coating slip.

As regards blade coating, it has been found that the Brookfield viscosity of the coating slip should not exceed 2500 cP. From samples 1, 2 and 3, it is seen that the viscosity of the coating slip increases with increasing admixture of polyvinyl alcohol as a carrier. At an admixture of 2 parts by weight of polyvinyl alcohol, the viscosity value became 2250 cP, i.e., on the way to the critical limit of 2500 cP. From sample 8, it is seen that an admixture of 1 part by weight of polyvinyl alcohol and 1 part by weight of carboxymethyl cellulose as a carrier gives a coating slip having a viscosity of as much as 6300 cP. This means that the coating slip is not useful in blade coating, i.e., it is not runnable. Then it is of no use that the coating slip has such a low value as 49 as regards the water-retention capacity. Sample 7 shows that an admixture of only a half part by weight of carboxymethyl cellulose (plus 1 part by weight of polyvinyl alcohol) as a carrier gives a slip having a low viscosity. Samples 4, 5 and 6, which constitute coating slips according to the invention, show that if the coating slip is supplied with sorbitol as a carrier in an increasing amount, the viscosity remains excellent, and it is even so that an admixture of 3 parts by weight of sorbitol as a carrier gives a coating slip having a viscosity that is considerably lower than the viscosity of a coating slip supplied with 1 part by weight of sorbitol as a carrier.

As regards the Hercules viscosity, it should be mentioned that also in that case (applies also to the capillary viscosity specified in FIGS. 1 and 2), the measurement results are obtained in the form of curves constructed from individual varying measuring points. The selection of a shear rate, viz. 17000 reciprocal seconds, and the corresponding viscosity value, is based on said curves. The Hercules viscosity of the different coating slips corresponds mainly to the Brookfield viscosity of the coating slips, even if the numerical values differ in magnitude. Considering samples 4, 5 and 6, i.e., the coating slips according to the invention, it is found that an increasing admixture of sorbitol as a carrier in the form of 1, 2 and 3 parts by weight results in a decreasing viscosity represented by the measured values 74.6, 69.2 and 63.6, respectively. This points out something that is very surprising, and to which there is not yet any explanation.

Figure 2:
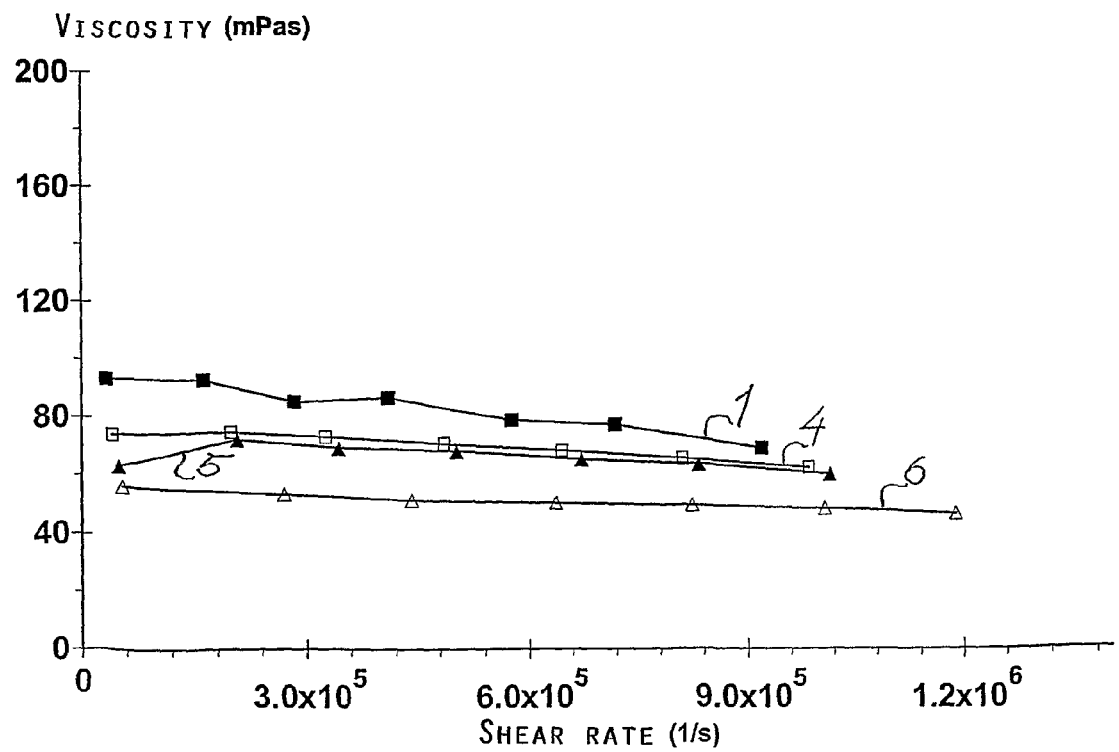
In FIG. 2, it is shown how the capillary viscosity of coating slips varies with the shear rate when using the carrier according to the invention, i.e., sorbitol, in the coating slip.

In FIGS. 1 and 2, the capillary viscosity of said coating slips is found. Here, the same pattern as previously is found. In FIG. 1, it is shown how an increasing use of polyvinyl alcohol as a carrier in the coating slip results in an increasing viscosity, and that the use of carboxymethyl cellulose in a low amount as a carrier in the coating slip even gives a low viscosity, while an increase to the double amount of carboxymethyl cellulose as a carrier in the coating slip increases the viscosity thereof dramatically, particularly at low shear rates. The coating slips according to the invention, i.e., 4, 5 and 6, and the viscosity curves thereof, are depicted collected in FIG. 2. As a comparison or reference, the viscosity curve of coating slip 1 has been included. Also in this type of viscosity measurement, it is established that an increasing admixture of sorbitol as a carrier in the coating slip results in a decreasing viscosity.

This embodiment example shows above all that usage of sorbitol as a carrier in coating slips (and then, there is a justified reason to assume that the same applies to surface sizes) stabilizes the fluorescent whitening agent (FWA) initially included in the coating slip, and then in the finished coating layer on paper in the usage thereof and over time in a marked way. Furthermore, said usage results in an apparent increase of the initial whiteness of the paper. Furthermore, the embodiment example shows that there is no sign of the usefulness and runnability of the coating slip being deteriorated by the admixture according to the invention, but the signs rather indicate the opposite.

The invention claimed is:

1. A method comprising the steps of:
   charging an amount of sorbitol as a carrier to a surface treatment size/coating slip; and surface treating a cardboard/paperboard to form a surface treatment layer by coating with the surface treatment size/coating slip;

wherein the amount of sorbitol charged as a carrier is an amount of 1-4 parts by weight, based on 100 parts by weight of pigments included in the coating slip.

2. The method according to claim 1, wherein the size/coating slip is in liquid form.

3. The method according to claim 1, wherein no other carrier is added to the size/coating slip resulting in sorbitol being the sole carrier.

4. The method according to claim 1, wherein at least one additional carrier is added to the size/coating slip.

5. The method according to claim 4, wherein in the case CMC is charged in addition to sorbitol as a carrier, CMC is charged in an amount that is less than 1 part by weight.

6. The method according to claim 4, wherein the at least one additional carrier is selected from the group consisting of carboxymethyl cellulose (CMC) and polyvinyl alcohol (PVA).

7. The method according to claim 6, wherein in the case CMC is charged in addition to sorbitol as a carrier, CMC is charged in an amount that is less than 1 part by weight.

8. The method according to claim 6 wherein CMC is charged in addition to sorbitol as a carrier, in an amount that is less than 1 part by weight.

9. The method according to claim 6, wherein PVA is charged in addition to sorbitol as a carrier, in an amount that does not exceed 2 parts by weight.

\* \* \* \* \*